(12) United States Patent
Gerber

(10) Patent No.: US 7,769,472 B2
(45) Date of Patent: Aug. 3, 2010

(54) ELECTRICAL STIMULATION LEAD WITH CONFORMABLE ARRAY OF ELECTRODES

(75) Inventor: Martin T. Gerber, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 201 days.

(21) Appl. No.: 11/194,041

(22) Filed: Jul. 29, 2005

(65) Prior Publication Data

US 2007/0027514 A1   Feb. 1, 2007

(51) Int. Cl.
*A61N 1/05* (2006.01)

(52) U.S. Cl. ...................................... 607/118

(58) Field of Classification Search ............. 607/116, 607/117, 118, 134, 135, 137, 138, 146; 600/393
See application file for complete search history.

(56) References Cited

U.S. PATENT DOCUMENTS

| | | | |
|---|---|---|---|
| 5,255,678 A | 10/1993 | Deslauriers et al. | |
| 5,255,679 A * | 10/1993 | Imran | 600/375 |
| 5,265,608 A | 11/1993 | Lee et al. | |
| 5,545,219 A | 8/1996 | Kuzma | |
| 5,840,076 A | 11/1998 | Swanson et al. | |
| 5,860,974 A | 1/1999 | Abele | |
| 6,266,568 B1 * | 7/2001 | Mann et al. | 607/137 |
| 6,529,777 B1 | 3/2003 | Holmström et al. | |
| 6,589,238 B2 | 7/2003 | Edwards et al. | |
| 6,600,955 B1 * | 7/2003 | Zierhofer | 607/57 |
| 6,889,093 B1 * | 5/2005 | Flammang | 607/122 |
| 6,895,283 B2 | 5/2005 | Erickson et al. | |
| 7,047,084 B2 * | 5/2006 | Erickson et al. | 607/116 |
| 7,099,718 B1 | 8/2006 | Thacker et al. | |
| 7,177,702 B2 * | 2/2007 | Wallace et al. | 607/117 |
| 7,181,288 B1 * | 2/2007 | Rezai et al. | 607/116 |
| 7,288,096 B2 | 10/2007 | Chin | |
| 2002/0156513 A1 | 10/2002 | Borkan | |
| 2003/0069623 A1 | 4/2003 | Stypulkowski | |
| 2003/0093130 A1 | 5/2003 | Stypulkowski | |
| 2003/0120328 A1 * | 6/2003 | Jenkins et al. | 607/116 |
| 2004/0059393 A1 * | 3/2004 | Policker et al. | 607/40 |
| 2004/0093053 A1 | 5/2004 | Gerber et al. | |
| 2004/0111139 A1 | 6/2004 | McCreery | |
| 2005/0060014 A1 | 3/2005 | Swoyer et al. | |
| 2005/0107861 A1 | 5/2005 | Harris et al. | |
| 2005/0222632 A1 | 10/2005 | Obino | |
| 2005/0246004 A1 | 11/2005 | Cameron et al. | |

(Continued)

OTHER PUBLICATIONS

U.S. Patent Application entitled "Electrical Stimulation Lead With Rounded Array of Electrodes", U.S. Appl. No. 11/194,087, filed Jul. 29, 2005.

(Continued)

*Primary Examiner*—George R Evanisko
*Assistant Examiner*—Amanda Patton
(74) *Attorney, Agent, or Firm*—Shumaker & Sieffert, P.A.

(57) ABSTRACT

An implantable electrical lead may include a conformable array of electrodes. The array of electrodes may be distributed across a rounded surface to position the electrodes in various positions and orientations relative to a target stimulation site. The lead may be useful in a variety of applications such as spinal cord stimulation to alleviate chronic pain, gastrointestinal stimulation to alleviate gastroparesis or obesity, pelvic floor stimulation to alleviate incontinence or sexual dysfunction, or deep brain stimulation to alleviate neurological disorders.

34 Claims, 7 Drawing Sheets

U.S. PATENT DOCUMENTS

2006/0079950 A1* 4/2006 Lehnhardt et al. ........... 607/137
2006/0241733 A1 10/2006 Zhang et al.
2006/0271137 A1* 11/2006 Stanton-Hicks ............. 607/118

OTHER PUBLICATIONS

Office Action dated Oct. 2, 2007 for U.S. Appl. No. 11/194,087 (8 pgs.).
Responsive Amendment for U.S. Appl. No. 11/194,087 (17 pgs.).
Office Action dated Mar. 4, 2008 for U.S. Appl. No. 11/194,087 (8 pgs.).
Response to Office Action dated May 8, 2008 for U.S. Appl. No. 11/194,087 (9 pgs.).
Office Action dated May 23, 2008 for U.S. Appl. No. 11/194,087 (10 pgs.).
Responsive Amendment dated Aug. 25, 2008 for U.S. Appl. No. 11/194,087 (12 pgs.).
Office Action dated Sep. 26, 2008 for U.S. Appl. No. 11/194,087 (8 pgs.).
Responsive Amendment dated Nov. 21, 2008 for U.S. Appl. No. 11/194,087 (12 pgs.).
Advisory Action dated Dec. 12, 2008 for U.S. Appl. No. 11/194,087 (4 pgs.).
Office Action dated Apr. 28, 2009 for U.S. Appl. No. 11/194,087 (6 pgs.).
Office Action dated Oct. 26, 2009 for U.S. Appl. No. 11/194,087 (8 pgs.).
Responsive Amendment dated Jul. 23, 2009 for U.S. Appl. No. 11/194,087 (11 pgs.).
Responsive Amendment dated Jan. 26, 2010 for U.S. Appl. No. 11/194,087 (11 pgs.).
Office Action dated Mar. 2, 2010 for U.S. Appl. No. 11/194,087 (7 pgs.).
Response dated May 3, 2010 for U.S. Appl. No. 11/194,087 (6 pgs.).

* cited by examiner

ELECTRICAL STIMULATION LEAD WITH CONFORMABLE ARRAY OF ELECTRODES

TECHNICAL FIELD

The invention relates to implantable medical devices and, more particularly, implantable electrical stimulators.

BACKGROUND

Electrical stimulation is an effective therapy for a variety of conditions and diseases that adversely affect patient health. For example, electrical stimulation has been effective in alleviating chronic pain, movement disorders, gastrointestinal disorders, and pelvic floor disorders. Spinal cord stimulation systems have been found to provide relief for chronic pain. Deep brain stimulation can be effective in treatment of movement disorders such as Parkinson's disease, as well as other neurological disorders such as epilepsy. Stimulation of the gastrointestinal tract can be effective in alleviating gastroparesis and obesity. Stimulation of the pelvic floor can be effective in alleviating urinary incontinence, fecal incontinence, pelvic pain, and sexual dysfunction.

Typically, electrical stimulation is delivered by an implantable pulse generator that is chronically implanted within the patient. One or more implantable leads extending from the implantable pulse generator carry electrodes for delivery of stimulation energy to a target tissue or nerve site. A lead typically carries a set of ring electrodes. Each ring electrode extends about the circumference of the lead, and is positioned at a respective axial position along the length of the lead. In operation, different combinations of electrodes, either on a single lead or among multiple leads, can be selected for delivery of electrical stimulation energy to the patient. Paddle leads also may be used.

The particular combinations and polarities of the electrodes may define the shape or direction of a stimulation pattern. Different combinations of electrodes may be tested to identify a configuration that provides suitable efficacy for the patient. Efficacy may be evaluated in terms of the degree of relief of symptoms of a targeted disorder and the severity of any side effects. The availability of multiple electrodes in the vicinity of a stimulation site increases the likelihood that an efficacious electrode combination will be identified. In addition, the electrode combination may be changed over the course of therapy to restore efficacy or explore other effective combinations. In some cases, selection of alternate electrode combinations may be necessary due to lead migration within the patient, progression of symptoms or an underlying ailment, or late onset of side effects.

SUMMARY

The invention is directed to an implantable electrical lead with a conformable array of electrodes. The array of electrodes may be distributed across a surface having a curved shape that positions the electrodes in various positions and orientations relative to a target stimulation site. The shape of the resulting electrode array may better conform to anatomical structures at a target stimulation site, and may be positionable to present different electrode array orientations to the stimulation site. For example, the lead may include a distal end with concave and convex surfaces over which electrodes are positioned.

The electrode array may include a flexible, conformable material. In some embodiments, the electrode array may be carried by a distal end that is inflatable to promote contact with, and possibly fixation at, a target stimulation site. In operation, the lead may be coupled to an electrical stimulator, which may be implantable or external. In addition to stimulation electrodes, the lead may carry one or more sensing electrodes. The lead may be useful in a variety of applications such as spinal cord stimulation to alleviate chronic pain, gastrointestinal stimulation to alleviate gastroparesis or obesity, pelvic floor stimulation to alleviate incontinence or sexual dysfunction, or deep brain stimulation to alleviate neurological disorders.

In one embodiment, the invention provides an implantable electrical stimulation lead comprising a lead body having a proximal end and a distal end, a plurality of electrical conductors within the lead body, and a plurality of stimulation electrodes positioned at the distal end of the lead body, each of the electrodes being coupled to at least one of the conductors. The distal end of the lead body has a substantially curved cross-section and defines at least one of a substantially concave surface and a substantially convex surface, and the electrodes are positioned at various positions on at least one of the concave surface and the convex surface.

In another embodiment, the invention provides an implantable electrical stimulator comprising an implantable pulse generator that generates electrical stimulation pulses, and an implantable lead coupled to the implantable pulse generator, the lead including lead body having a proximal end and a distal end, a plurality of electrical conductors within the lead body, and a plurality of stimulation electrodes positioned at the distal end of the lead body, each of the electrodes being coupled to at least one of the conductors, wherein the distal end of the lead body has a substantially curved cross-section and defines at least one of a substantially concave surface and a substantially convex surface, and the electrodes are positioned at various positions on at least one of the concave surface and the convex surface.

In another embodiment, the invention provides a method comprising applying electrical stimulation pulses to a patient via an implanted lead, wherein the lead comprises a lead body having a proximal end and a distal end, a plurality of electrical conductors within the lead body, and a plurality of stimulation electrodes positioned at the distal end of the lead body, each of the electrodes being coupled to at least one of the conductors, and wherein the distal end of the lead body has a substantially curved cross-section and defines at least one of a substantially concave surface and a substantially convex surface, and the electrodes are positioned at various positions on at least one of the concave surface and the convex surface.

In an additional embodiment, the invention provides an implantable electrical stimulation lead comprising a lead body having a proximal end and a distal end, a plurality of electrical conductors within the lead body, and a plurality of stimulation electrodes positioned at the distal end of the lead body, each of the electrodes being coupled to at least one of the conductors. The distal end of the lead body is substantially pliant and conformable to a target stimulation site.

In a further embodiment, the invention provides an implantable electrical stimulation lead comprising a lead body having a proximal end and a distal end, a plurality of electrical conductors within the lead body, and a plurality of stimulation electrodes positioned at the distal end of the lead body, each of the electrodes being coupled to at least one of the conductors. The distal end of the lead body defines a first distal member and a second distal member extending from the lead body, the first and second distal members defining portions a channel-like region, wherein the electrodes are positioned at various positions on each of the first and second distal members.

In various embodiments, the invention may provide one or more advantages. For example, distribution of the array of electrodes across a conformable surface may increase the spatial diversity of the electrodes. In particular, the conformable surface may provide a greater variety of distances, angles, and surface contact between the electrode array and a target stimulation site, relative to ordinary ring electrodes or paddle electrodes. Increased spatial diversity among the electrodes may increase the likelihood of obtaining an electrode combination that engages the target stimulation site in a way that supports efficacy. In some cases, the distribution of electrodes over a conformable surface may present a greater number of options for efficacious stimulation, both at the time of implant and post-implant. Spatial diversity among the electrodes may be especially advantageous in applications in which deployment of a lead within a stimulation site can be difficult, such as within the sacrum.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
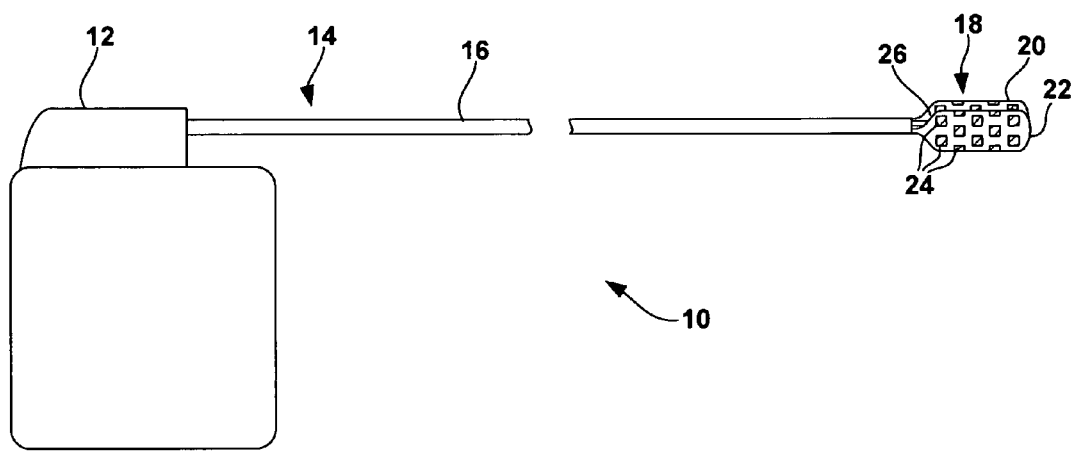
FIG. 1 is a schematic diagram illustrating an implantable electrical stimulation system incorporating a pulse generator and a lead with a conformable array of electrodes.

FIG. 1 is a schematic diagram illustrating an implantable electrical stimulation system 10 incorporating a stimulator 12 and a lead 14 with a conformable array of electrodes. As shown in FIG. 1, system 10 includes an implantable electrical stimulator 12 coupled to an implantable lead 14. Stimulator 12, which may also be referred to as an implantable pulse generator (IPG), may be a neurostimulator that generates neurostimulation pulses for delivery to a target stimulation site via lead 14. In some cases, lead 14 alternatively may be used in conjunction with an external electrical stimulator, e.g., for percutaneous or trial stimulation. In either case, lead 14 may be surgically or percutaneously implanted within a patient.

Lead 14 includes a lead body 16 having a proximal end coupled to stimulator 12 and a distal end 18. Lead body 16 carries a plurality of electrical conductors (not shown). In the example of FIG. 1, distal end 18 defines a concave surface 20 and a convex surface 22. A plurality of stimulation electrodes 24 are positioned at distal end 18 of lead body 16. Concave surface 20 forms a trough- or channel-like region 26. Electrodes 24 may be positioned on convex surface 20, concave surface 22 or both. Each of the electrodes 24 is coupled to one or more of the electrical conductors within lead body 16. The conductors electrically couple the electrodes to stimulation pulse generation circuitry within stimulator 12. Upon implantation, lead 14 places electrodes 24 in close proximity to a target stimulation site for delivery of stimulation pulses to the patient.

Electrodes 24 are positioned at various positions across the concave and convex surfaces 20, 22 defined by the distal end 18 of lead body 16. Concave and convex surfaces 20, 22 provide a variety of orientations and angles for presentation of electrodes 24 to a stimulation site. By rotating lead body 16, for example, the presentation of electrodes 24, in terms of orientation, angle, and distance to a target stimulation site, may be significantly modified. In this manner, distal end 18 provides greater spatial diversity among the electrodes 24, and can be positioned to enhance conformance between the electrode array and the target stimulation site. Pulse generator 12 may deliver stimulation pulses across two or more electrodes 24 on concave surface 20, two or more electrodes on convex surface 22, or between two of more electrodes on both concave and convex surfaces 20, 22.

Distribution of the array of electrodes 24 across a curved, conformable surface or surfaces provides a greater variety of distances, angles, and surface contact between the electrode array and a target stimulation site, relative to ordinary ring electrodes or paddle electrodes. The shape and configuration of distal end 18 may also permit a greater number of separate electrodes to be provided. Increased spatial diversity among the electrodes 24, and the ability to rotate lead 16 to change the orientation of the electrode array, may increase the likelihood of obtaining an electrode combination that engages the target stimulation site in a way that supports efficacy. In some cases, the distribution of electrodes 24 as shown in FIG. 1 may present a greater number of options for efficacious stimulation. Spatial diversity among the electrodes 24 may be especially advantageous in applications in which deployment of a lead within a stimulation site can be difficult, such as within the sacrum.

Figure 3:
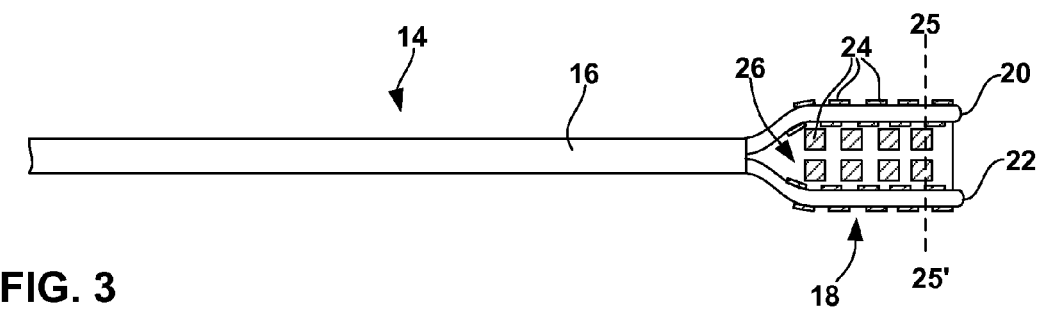
FIG. 3 is a top view of the lead of FIG. 1.
Figure 4:
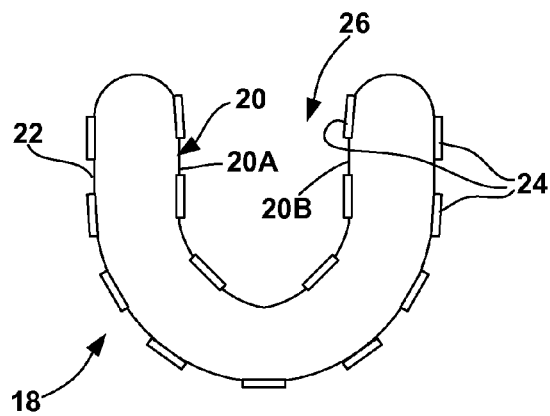
FIG. 4 is a cross-sectional front view of a distal end of the lead of FIGS. 2 and 3.
Figure 5:
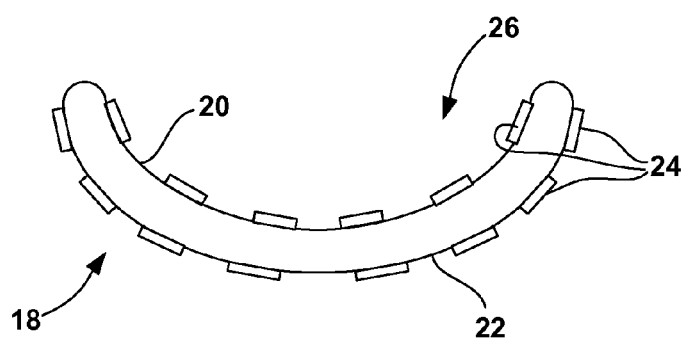
FIG. 5 is a cross-sectional front view of a distal end of the lead of FIGS. 2 and 3 in accordance with an alternative embodiment.

The channel-like region 26 defined by concave surface 20 may permit the electrode array to engage a nerve site on multiple sides, providing a "wrapping" effect. In other words, channel-like region 26 may receive nerve tissue and laterally engage the nerve tissue with electrodes 24 carried on the concave surface 20, thereby enveloping a substantial surface area of the nerve site among electrodes 24. In some cases, channel-like region 26 may be applied laterally to engage a particular nerve fiber such that stimulation pulses can be applied directly across the nerve fiber between electrodes 24 disposed on concave surface 20, at opposite sides of channel-like region 26. As shown in FIG. 3-5, concave surface 20 may be a continuous surface that defines channel-like region 26. In this manner, concave surface 20 may have a structurally continuous cross-section, e.g., as shown in FIGS. 4 and 5, that defines a substantially continuous channel-like region 26.

In some embodiments, one or more electrodes 24 may be used for sensing, rather than stimulation. In particular, some electrodes 24 may be used to sense electrical potentials in a region adjacent a stimulation site. The sensed electrical potentials may be action potentials created intrinsically by the patient, either autonomously or in response to application of stimulation pulses. In this case, stimulator 12 may process the sensed electrical potentials for diagnostic purposes or for adjustment of stimulation pulses delivered to the patient. Alternatively, the sensed electrical potentials may be the potentials associated with the stimulation pulses delivered to the patient. The sensed stimulation pulse potentials may be processed to determine actual energy delivered to the patient, in order to increase or decrease the amplitude, pulse width or pulse rate of stimulation pulses.

Figure 2:
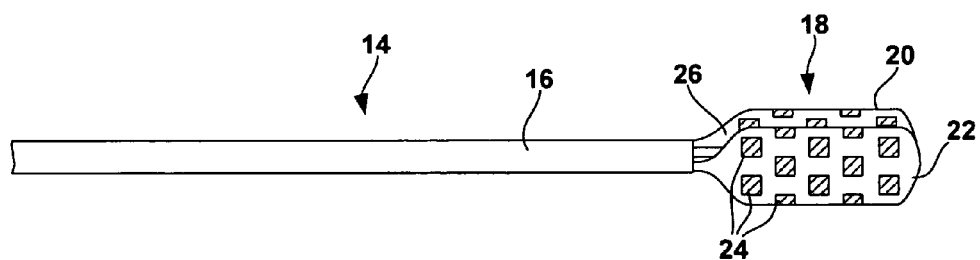
FIG. 2 is an enlarged side view illustrating the lead of FIG. 1.
Figure 6:
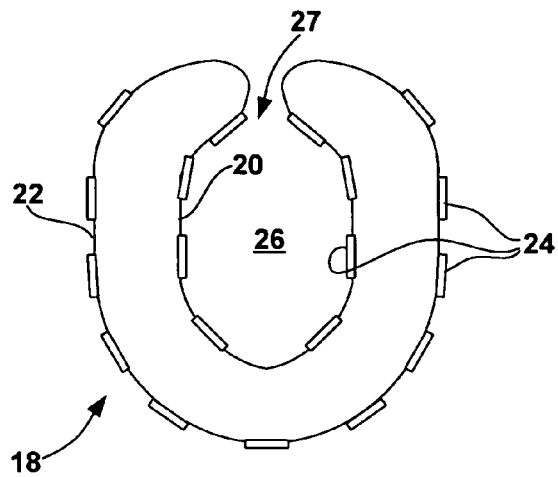
FIG. 6 is a cross-sectional front view of a distal end of the lead of FIGS. 2 and 3 in accordance with another alternative embodiment.

FIG. 2 is an enlarged schematic diagram illustrating lead 14 of FIG. 1. FIG. 3 is a top view of lead 14 of FIG. 1. The view of FIG. 3 is rotated approximately ninety degrees about the longitudinal axis of lead body 16, relative to the view of FIG. 2. FIG. 4 is a cross-sectional front view of distal end 18 of lead 14 of FIG. 3, taken along line 25-25'. FIG. 5 is a cross-sectional front view of a distal end 18 of lead 14 of FIG. 3, taken along line 25-25', in accordance with an alternative embodiment. FIG. 6 is a cross-sectional front view of a distal end 18 of lead 14 of FIG. 3, taken along line 25-25', in accordance with another alternative embodiment.

As shown in FIGS. 2-6, electrodes 24 may be distributed across substantially the entire rounded concave surface 20 and convex surface 22 of distal end 18 of lead 14. For example, electrodes 24 may be positioned around an entire lateral circumference of convex surface 22, as well as on concave surface 20 within channel-like region 26. In the example shown in FIG. 4, concave surface 20 defines a first portion 20A and a second portion 20B that faces toward first portion 20A. In FIG. 4, electrodes 24 are positioned on both first portion 20A and second portion 20B of concave surface 20. Alternatively, in other embodiments, electrodes 24 may be positioned on selected portions of concave and convex surfaces 20, 22, or on one of the concave or convex surface, but not the other. In addition, electrodes 24 may be distributed in a generally regular or irregular pattern across concave surface 20 and convex surface 22.

Distal end 18 of lead 14 may have a generally curved or arcuate cross-section. In the example of FIG. 4, distal end has a generally U-shaped cross-section. In the alternative embodiment of FIG. 5, the cross-section of distal end 18 is wider and more arch-like than the cross-section shown in FIG. 4. In the alternative embodiment of FIG. 6, the cross-section of distal end 18 is generally ring-like, but includes an access gap 27. Other cross-sectional shapes are possible, such as V-shaped cross-sections, horse-shoe shaped cross-sections, and the like. Such cross-sections may be generally curved or arcuate in cross-section so as to define a concave surface and a convex surface. In embodiments in which distal end 18 of lead 14 defines a concave surface 20, concave surface 20 may be a continuous surface. In general, concave surface 20 permits electrodes 24 to receive nerve tissue, muscle tissue, or other tissue in the target stimulation site. In some cases, target tissue may be at least partially wrapped or enveloped within channel-like region 26.

Convex surface 22 provides a rounded surface for engagement with contoured surfaces. By rotating lead body 16 relative to the target tissue, different electrodes 24 carried on concave surface 20, convex surface 22, or both, may be brought into contact with the target tissue. In this manner, lead 14 provides a vast array of options for presentation of electrodes 24 to the target tissue, as well as a many options for selection of different electrode groups, combinations, or polarities (e.g., using an external programmer) for delivery of stimulation pulses following implantation of the lead within a patient.

In the example of FIG. 6, gap 27 may permit entry of a nerve fiber or other target tissue into channel 26. During entry into gap 27, the portions of distal end 18 adjacent gap 27 may spread apart to permit passage of tissue. After the tissue has passed into channel-like region 26, the portions of distal end 18 adjacent gap 27 may spring back toward their original position, serving to capture the tissue within the channel-like region. In this example, concave surface 20 may present an array of electrodes 27 that covers at least 180 degrees, and possibly 270 degrees, circumferentially around the tissue captured within channel-like region 26.

Distal end 18, including concave surface 20 and convex surface 22, may be integrally formed with lead body 16, e.g., by molding, casting or the like. Alternatively, distal end 18 may be separately fabricated and attached to lead body 16, e.g., by crimping, adhesive bonding, ultrasonic welding, or the like. In general, distal end 18 and lead body 16 may be formed of biocompatible polymeric materials such as polyurethane or silicone, or a combination of such materials. In some embodiments, distal end 18 is soft, pliant and conformable to permit the concave surface 20 and convex surface 22, and electrodes 24, to better conform to anatomical structures within a target stimulation site.

The use of pliant materials, such as silicone, may permit the U-shaped, arc-shaped, ring-shaped or other curved cross-section of distal end 18 to spread apart for engagement of tissue within channel-like region 26. In some cases, the material may be substantially elastomeric, such that the material has at least some elasticity. Also, in some embodiments, distal end 18 may include a supporting frame to bias the distal end into a desired shape, as will be described in greater detail below. Upon engagement of tissue within channel-like region 26 by spreading distal end 18 apart, elastomeric material may cause distal end 18 to spring back and provide a slight compressive fit to the captured tissue. In this case, a relatively large number of electrodes 24 on concave surface 20 may be engaged with the tissue for electrically conductive coupling of stimulation pulses. In particular, the elastomeric property may enhance coupling pressure between electrodes 24 and tissue.

Likewise, when distal end 18 is tunneled into a relatively narrow stimulation site, distal end 18 may bend inward such that the channel-like region 26 temporarily narrows and the outer cross-sectional width of distal end 18 becomes smaller. Distal end 18 and lead body 16 may accommodate a stylet to guide and steer lead 14 for implantation. A distal tip of the stylet may extend into distal end 18 to temporariliy provide distal end with sufficient column strength to support tunneling. Dilators, sheaths and the like may be used for percutaneous implantation of lead 14. However, lead 14 alternatively may be surgically implanted, i.e., by an open incision surgical procedure without substantial tunneling. An elastomeric material may cause distal end 18 to spring back toward the original cross-section width, and exert an outward force against surrounding tissue. In this manner, a relatively large number of electrodes 24 on convex surface 22 may be engaged within tissue for electrically conductive coupling of stimulation pulses. At the same time, outward force may serve to at least partially anchor, or prevent significant migration of, distal end 18 of lead 14.

In general, the length, width and thickness of distal end 18 may vary according to different stimulation applications and, in particular, different anatomical characteristics, including sizes and geometries, presented by pertinent implant sites. As an example, distal end 18, which extends from lead body 16 and defines the concave and convex surfaces 20, 22, may have a length (along the longitudinal axis of lead body 16) in a range of approximately 2 to 15 mm, a width (generally transverse to the longitudinal axis of lead body 16) in a range of approximately 1 to 5 mm, and a height (transverse to width) in a range of approximately 1 to 5 mm.

Electrodes 24 may be formed as conductive elements, such as conductive metal pads, that are formed on or within concave surface 20 and convex surface 22. Electrodes 24 may be formed from a variety of electrically conductive, biocompatible materials. The shape of electrodes 24 may be circular, oval, rectangular, square, or irregular. Example electrode materials include platinum and platinum iridium. Electrodes 24 may be printed or otherwise deposited on surfaces 20, 22 at selected positions. Alternatively, electrodes 24 may be fabricated and embedded into surfaces 20, 22, e.g., by casting or insert molding. In either case, conductors within lead body 16 may be crimped, soldered, welded, wire bonded or otherwise attached to electrodes 24, through the material of distal end 18, to form an electrical connection.

As a further alternative, conductors may be formed as conductive traces within distal end 18. In particular, conductors may be printed on an interior surface opposite corresponding electrodes, and electrical connections can be made by through holes, i.e., vias, and conductive plating. For example, distal end 18 may be formed as a multi-layer structure with multiple layers of flexible polymeric material carrying printed conductive traces and electrodes. The multiple layers may initially be printed as flat, individual layers and then layed up together into a multi-layer stack. The multi-layer stack may include a biasing layer that carries a supporting frame. The supporting frame biases the multi-layer stack into a desired shape, such as the U-shaped, arc-shaped, or ring-shaped configurations shown in FIGS. 4-6. Examples of suitable materials for the frame are titanium, stainless steel or shape memory alloys such as Nitinol.

Figure 7:
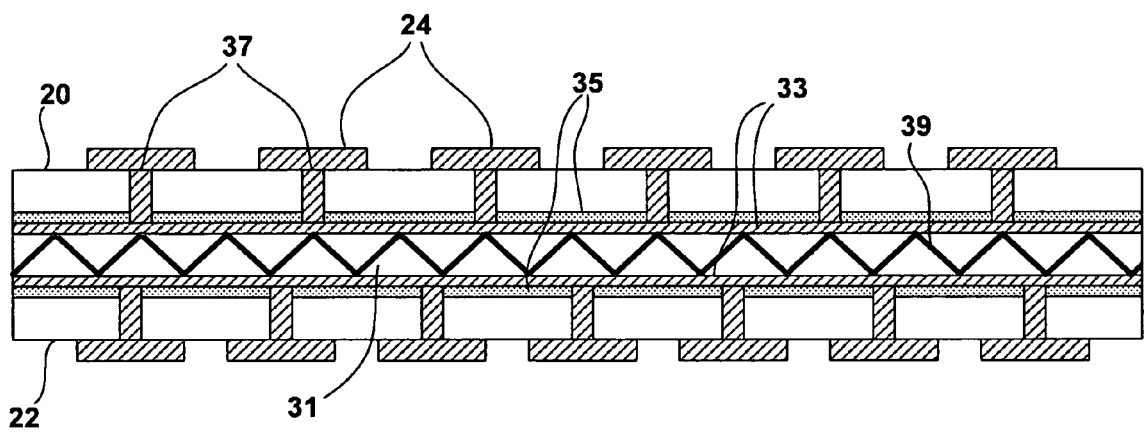
FIG. 7 is a cross-sectional side view of a multi-layer structure that may be used to form a conformable array of electrodes.
Figure 8:
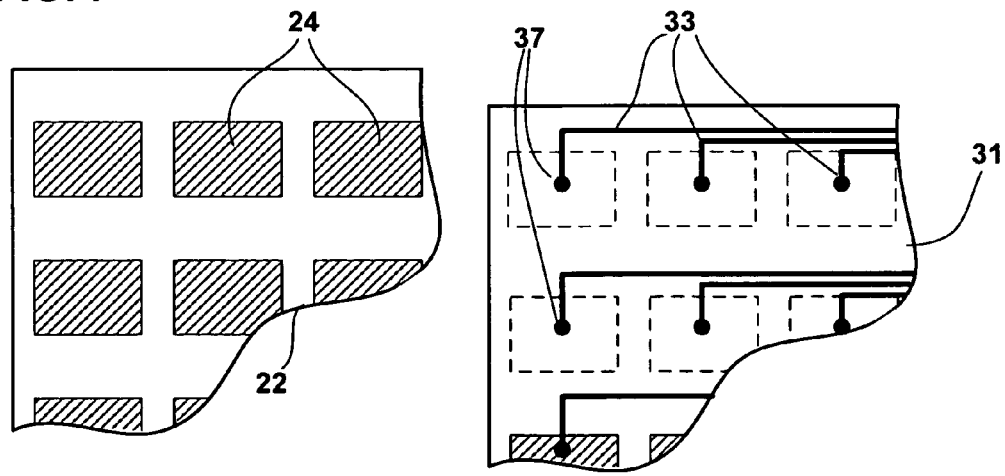
FIG. 8 is a plan view of individual layers within the multi-layer structure of FIG. 7.

FIG. 7 is a cross-sectional side view of a multi-layer structure that may be used to form a conformable array of electrodes. FIG. 8 is a plan view of individual layers within the multi-layer structure of FIG. 7. As shown in FIG. 7, the multi-layer structure may include conformable polymeric layers corresponding to concave surface 20 and convex surface 22. Each surface 20, 22 carries an array of electrodes 24, which may be printed or otherwise deposited in a desired pattern while the respective surfaces are laid out flat. Electrodes 24 may have common or different sizes and be positioned in regular or irregular patterns. Although surfaces 20, 22 may be laid out flat for fabrication, they are still referred to as concave and convex, respectively, for convenience. A center layer 31 carries electrically conductive material 33 on opposing sides. The conductive material 33 may be etched away from center layer 31 to form conductive traces. Alternatively, conductive material 33 may be printed or otherwise deposited on center layer 31.

Center layer 31 may be formed from a flexible, polymeric material such as silicone or polyurethane. The multi-layer circuit may be formed in a manner similar to fabrication of a flex circuit. Additional flexible layers may be provided to enhance conformability. In some embodiments, regions between adjacent layers may be filled, e.g., by injection or coating, with an elastomeric material, such as silicone, to further enhance conformability. The elastomeric material may be cured following formation to partially harden the material, e.g., by application of heat, pressure or radiation. Alternatively, a fluid such as silicone may be allowed to remain in a semi-liquid or gel form, enhancing conformability.

The conductive material 33 carried by center layer 31 may be bonded to concave surface 20 and convex surface by an adhesive layer 35. Conductive through-holes 37, i.e., vias, are formed to couple selected traces of conductive material 33 to selected electrodes 24 on concave and convex surfaces 20, 22, as shown in FIGS. 7 and 8. The traces of conductive material 33 may be coupled, at a proximal edge of distal end 18, to corresponding axial or coiled conductors that extend along the length of lead body 16 for electrical connection to stimulator 12.

As further shown in FIG. 7, a supporting frame 39 may be embedded in the multi-layer stack, e.g., within center layer 31. The supporting frame 39 may be configured to bias the multi-layer stack into a desired shape upon completion of the fabrication of electrodes 24, traces of conductive material 33, and vias 37. As mentioned previously, the supporting frame 39 may be fabricated from a biocompatible metal such as titanium, stainless steel or a shape memory alloy such as Nitinol. Once the multi-layer structure of distal end 18 is released from a manufacturing jig, the supporting frame 39 causes distal end 18 to assume the desired shape. At this point, distal end 18 may be attached to lead body 16. Alternatively, additional processing may be performed, such as milling of the multi-layer structure to remove excess polymeric material. Other techniques may be used to bias the shape of distal end 18, such as differential tensioning of particular layers within the multi-layer stack to cause a particular shape to be assumed.

As mentioned above, conductive traces within distal end 18 may be electrically coupled to respective conductors within lead body 16, e.g., by soldering, crimping, welding, wire bonding, or the like. The conductors extend axially or as helical coils along the length of lead body 16. In some cases, the use of coiled conductors may provide enhanced structural integrity. Coiled conductors are wound in a helical coil, e.g., at alternating turns, such that multiple conductors can be coiled together. At distal end 18 of lead body 16, the conductors are coupled, via the traces, to respective electrodes 24. At a proximal end of lead body 16, the conductors are coupled to the output of stimulation pulse generator circuitry. The conductors may be formed from any of a variety of flexible, electrically conductive materials. One example is MP35N™ alloy, which is a biocompatible, nonmagnetic, nickel-cobalt-chromium-molybdenum alloy with high strength and corrosion resistance, and a silver core to improve conductance. Lead 14 may include at least eight, at least sixteen, or at least thirty-two axial or coiled conductors and associated electrodes 24.

The number of electrodes 24 may vary according to a given stimulation application. In some embodiments, lead 14 may include eight, sixteen, thirty-two or more electrodes 24 to provide a large number of independently accessible stimulation orientations within a target stimulation site. For some stimulation applications, such as spinal cord stimulation or stimulation of the sacral or pudendal nerves, distal end 18 may have an overall surface area in a range of approximately 12 to 470 square mm. The surface area of concave surface 20 may be in a range of approximately 6 to 235 square mm, while the surface area of convex surface 22 may be in a range of approximately 6 to 235 square mm. Lead body 16 may have a substantially uniform outer diameter of approximately 1 to 5 mm.

Given an overall surface area of approximately 12 to 470 square mm, each electrode 24 may have a surface area of approximately 0.25 to 50 square mm. Electrodes of the size and number described above should provide a relatively large number of independently accessible stimulation sites while leaving sufficient spacing between electrodes to avoid excessive redundancy. The above dimensions may vary according to the application envisioned for lead 14. Electrodes 24 may have the same size or different sizes. For example, different electrode sizes may be appropriate depending on the position of an electrode 24, the use of an electrode as stimulation or sensing electrode, or the use of the electrode as an anodic or cathodic electrode.

Figure 9:
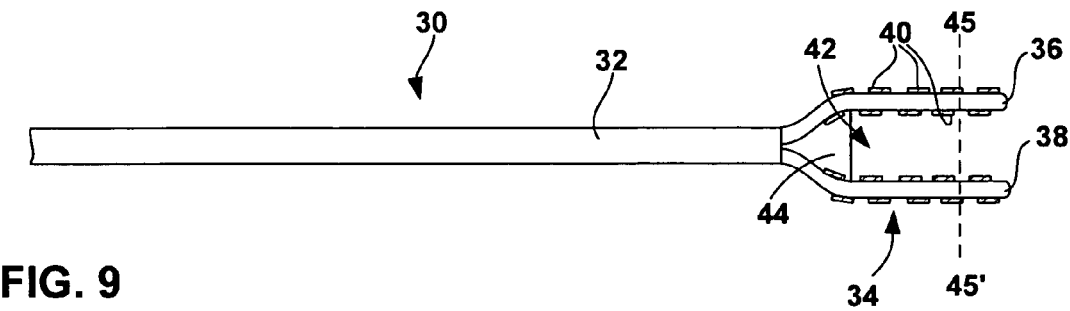
FIG. 9 is a top view of an alternative embodiment of the lead of FIGS. 2 and 3.
Figure 10:
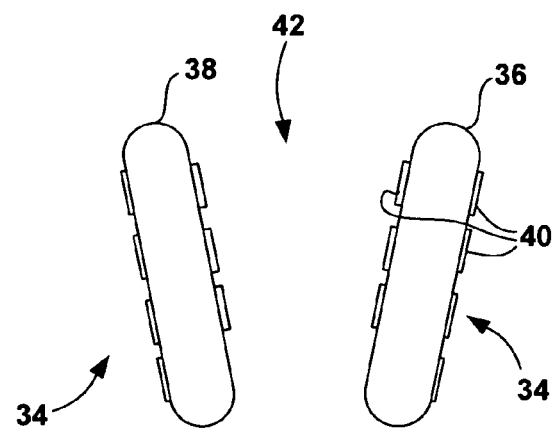
FIG. 10 is a cross-sectional front view of a distal end of the lead of FIG. 9.

FIG. 9 is a top view of an alternative embodiment of the lead of FIGS. 2 and 3. In the example of FIG. 9, a lead 30 includes a lead body 32 and a distal end 34. FIG. 10 is a cross-sectional front view of a distal end 34 of lead 30 of FIG. 9 taken along line 45-45'. Distal end 34 includes first and second distal members 36, 38 that extend distally forward from lead body 32. In contrast to the embodiment illustrated in FIGS. 2 and 3, distal members 36, 38 form separate arm-like portions of distal end 34 rather than a continuous, concave surface, and may define a Y or tuning fork shape. Electrodes 40 are carried on inner and outer surfaces of distal members 36, 38. Distal members 36 and 38 define a channel-like region 42, and may include a web portion 44 that partially joins the distal members. However, in contrast to the embodiment illustrated in FIGS. 2 and 3 that includes a concave surface, distal members 36, 38 may be structurally independent. Manufacturing processes similar to those described above may be used for distal member 34 of FIGS. 9 and 10.

As in other embodiments described herein, distal end 34 of lead 30 may be formed of conformable materials and may include a supporting frame to achieve a desired shape. In general, distal end 34 permits presentation of the array of electrodes 40 to a stimulation site with a variety of orientations, angles and distances. In addition, distal members 36, 38 can be manipulated to capture tissue or even nerve fibers within channel-like region 42. Incorporation of elastomeric material or an elastic or shape memory supporting frame may permit distal members 36, 38 to flex inward or outward for presentation to a stimulation site, but then bias the distal members toward their original positions to promote fixation, enhance electrical coupling pressure, or both.

Figure 11:
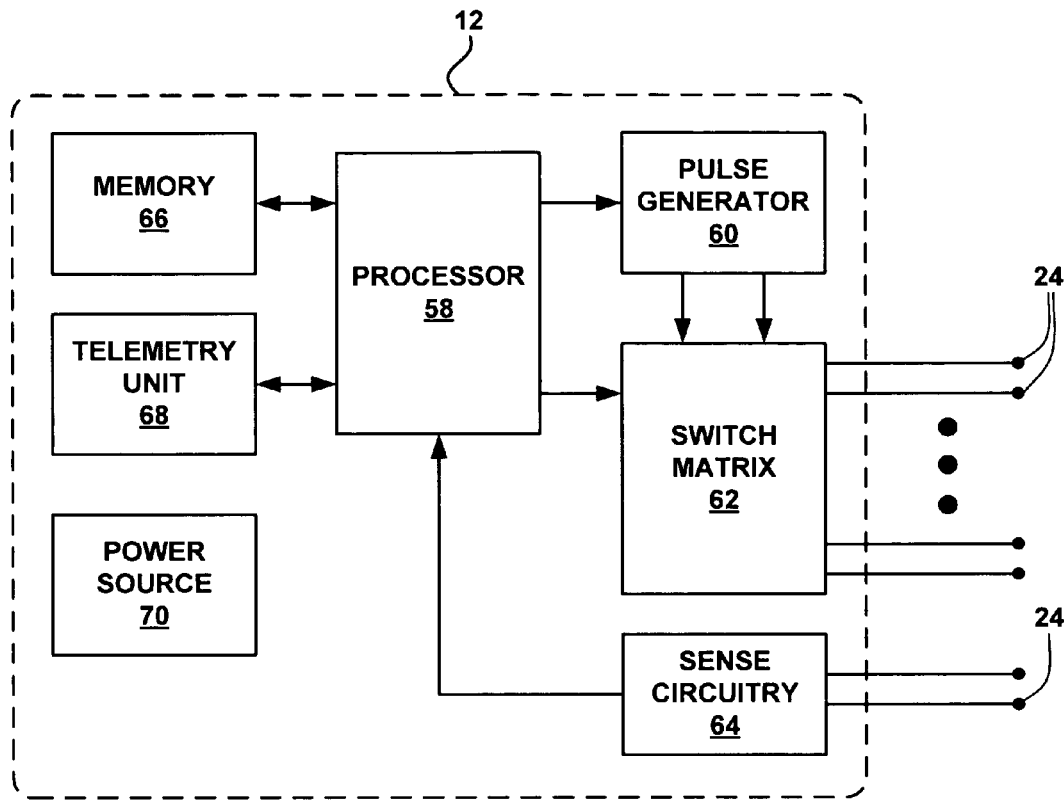
FIG. 11 is a block diagram illustrating exemplary components of an implantable electrical stimulator.

FIG. 11 is a block diagram illustrating exemplary components of an implantable electrical stimulator 12. Stimulator 12 may be used in conjunction with lead 14, as depicted in any of FIGS. 1-6, or lead 30 of FIGS. 9 and 10, as well as with leads constructed according to other embodiments described herein. As shown in FIG. 11, stimulator 12 may include a processor 58, pulse generator 60, switch matrix 62, sense circuitry 64, memory 66 telemetry unit 68, and power source 70. Stimulator 12 has a biocompatible housing, e.g., of titanium or stainless steel. Pulse generator 60 generates electrical stimulation pulses at an amplitude (voltage or current), pulse width and pulse rate determined by processor 58. Sense circuitry 64 is optional, and processes sensed electrical potentials obtained by a subset of the electrodes 24 carried by lead 14.

The amplitude, pulse width and pulse rate parameters of stimulation pulses delivered by pulse generator 60 are selected to address any of a variety of symptoms or disorders. For example, pulse generator 60 may produce stimulation pulses with parameters selected to alleviate chronic pain, gastrointestinal disorders such as gastroparesis or obesity, and pelvic floor disorders such as incontinence, sexual dysfunction or pain. Accordingly, the stimulation pulses may be applied to the spinal cord, gastrointestinal tract, sacral nerves or pudendal nerves. Additional applications may include peripheral nerve stimulation. The pulses also may be used in conjunction with a lead as described herein to provide deep brain stimulation for alleviation of movement disorders such as Parkinson's disease, as well as other neurological disorders such as epilepsy.

An exemplary range of neurostimulation stimulation pulse parameters likely to be effective in alleviating symptoms of one or more of chronic pain, a gastrointestinal disorder, a urinary tract disorder such as incontinence, or sexual dysfunction, are as follows:

1. Frequency: between approximately 0.5 Hz and 500 Hz, more preferably between approximately 5 Hz and 250 Hz, and still more preferably between approximately 10 Hz and 50 Hz.

2. Amplitude: between approximately 0.1 volts and 50 volts, more preferably between approximately 0.5 volts and 20 volts, and still more preferably between approximately 1 volt and 10 volts.

3. Pulse Width: between about 10 microseconds and 5000 microseconds, more preferably between approximately 62 microseconds and 620 microseconds, and still more preferably between approximately 180 microseconds and 450 microseconds.

Switch matrix 62 applies stimulation pulses generated by pulse generator 60 across selected electrodes 24 within a lead 14, or within two or more leads. The stimulation pulses may be applied in a bipolar or multipolar arrangement, in which multiple electrodes 24 are selected for delivery of stimulation pulses, e.g., across or among different electrode pairs or groups. Alternatively, in some cases, stimulation pulses may be applied in a unipolar arrangement, in which stimulation pulses are applied between a single electrode 24 selected from the electrodes 24, and a reference electrode carried by the housing of stimulator 12.

Processor 58 specifies electrode combinations and respective electrode polarities. Stimulation pulses may be applied across two electrodes 24, as anode and cathode, or across multiple electrodes with different electrodes designated as anodes and cathodes. In response to electrode combinations and polarities specified by processor 58, switch matrix 62 applies the stimulation pulses to the appropriate electrodes 24 via conductors carried in lead body 16. As an alternative to switch matrix 62, in some embodiments, stimulator 12 may include multiple pulse generators 60, each coupled to a given electrode or across a given electrode pair.

Memory 66 stores instructions for execution by processor 58 to control pulse generator 60 and switch matrix 62. For example, memory 66 may store programs defining different sets of stimulation parameters and electrode combinations. Memory 66 also may store operational information relating to operation of stimulator 12. Memory 66 may include any form of computer-readable media such as random access memory (RAM), read only memory (ROM), electronically programmable memory (EPROM or EEPROM), or flash memory, or any combination thereof. Processor 58 may be realized by one or more microprocessors, digital signal processors (DSPs), Application-Specific Integrated Circuits (ASIC), Field-Programmable Gate Arrays (FPGA), or other equivalent integrated or discrete logic circuitry.

Telemetry unit 68 supports wireless communication between stimulator 12 and an external programmer. Processor 58 controls telemetry unit 68 to receive programming information and send operational information. Programming information may be received from an external clinician programmer or an external patient programmer. Wireless telemetry may be accomplished by radio frequency (RF) communication or proximal inductive interaction with a programmer.

Power source 70 delivers operating power to the components of stimulator 12. Power source 70 may include a rechargeable or nonrechargeable battery and a power generation circuit to produce the operating power. In some embodiments, battery recharging may be accomplished through proximal inductive interaction between an external charger and an inductive charging coil within stimulator 12. In other embodiments, operating power may be derived by transcutaneous inductive power generation, e.g., without a battery.

Sense circuitry 64 may be provided, in some embodiments, to process electrical potentials sensed by a subset of the electrodes 24. In particular, some electrodes 24 may be used to sense electrical potentials in a region adjacent a stimulation site, either for diagnostic purposes or closed loop control of stimulation pulse parameters. Electrical potentials may be sensed across two or more sense electrodes, or between one electrode carried by lead 14 and a reference electrode carried by a housing associated with stimulator 12. The electrical potentials obtained by sense circuitry 64 may be stored in memory 66. With sense circuitry 64, lead 14 may include both stimulation electrodes and sense electrodes.

Figure 12:
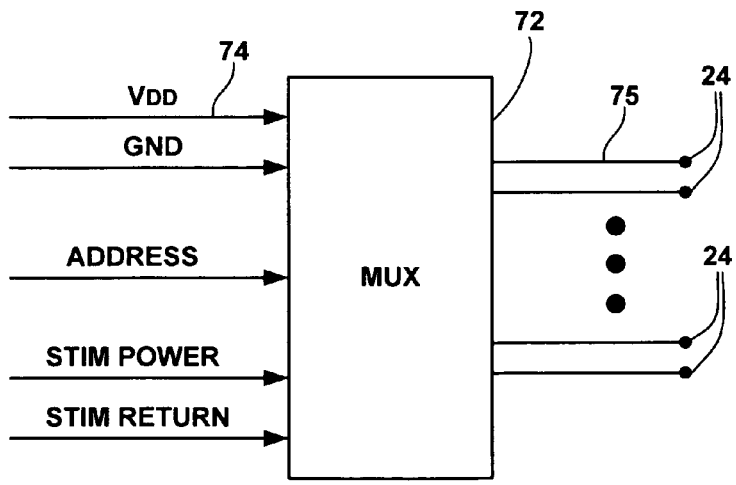
FIG. 12 is a block diagram illustrating a multiplexer (MUX) arrangement for use with a lead as described herein.

FIG. 12 is a block diagram illustrating a multiplexer (MUX) arrangement for use with a lead as described herein. In some embodiments, a lead body 16 may include a multiplexer (MUX) chip 72 adjacent distal end 18 of lead 14. In this case, lead body 16 may contain a set of input conductors 74 that extend from a proximal end of lead 14 to the MUX chip 72, and a set of output conductors 75 that extend from the MUX chip to respective electrodes 24. The number of output conductors 75 corresponds to the number of electrodes 24, as there is one output conductor for each electrode 24. However, the number of output conductors 75 is greater than the number of input conductors 74. The use of a MUX chip 72 within lead body 16 can reduce the number of input conductors 74 that must extend along the entire length of the lead body.

With the MUX chip 72 placed near distal end 18, the number of input conductors 74 that must extend along substantially the entire length of lead body 16 can be reduced. For example, the input conductors 74 may include a chip power conductor VDD, a chip ground conductor GND, a serial addressing conductor ADDRESS, a stimulation power conductor STIM POWER, and a stimulation return conductor STIM return. The chip power and chip ground conductors VDD, GND deliver operating power to MUX chip 72. The stimulation power and return conductors deliver stimulation pulses for application across a set of electrodes 24 in distal end 18 of lead 14, via output conductors 75. The serial addressing conductor carries a serial codeword that identifies a combination of electrodes for application of stimulation pulses. In response to the codeword, MUX chip 72 configures a switch matrix to direct the stimulation pulses across the specified combination of two or more electrodes. The codeword may be transmitted by pulse width modulation or other serial bus schemes, and may specify the electrodes to be included in an electrode combination, as well as the polarities of the electrodes. In response to the address codeword, MUX chip 72 applies the stimulation current across the specified set of electrodes 24 by selecting appropriate output conductors 75.

Figure 13:
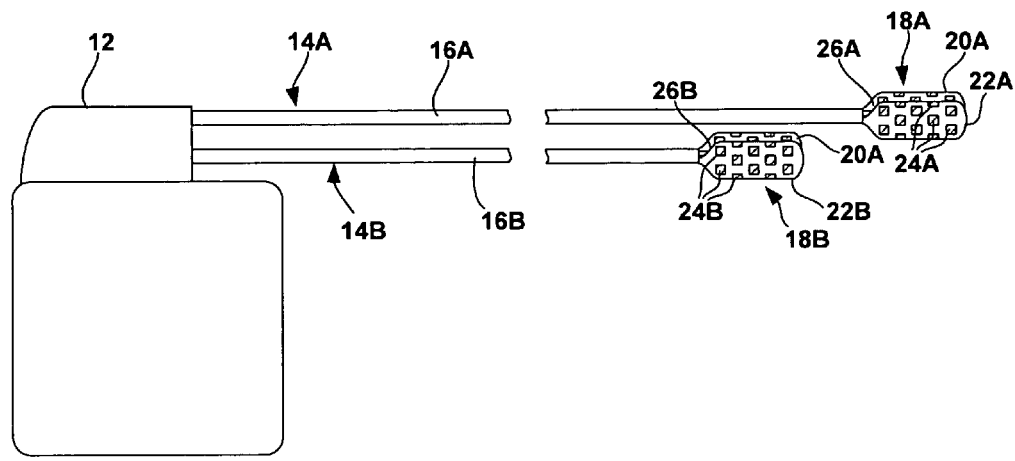
FIG. 13 is a schematic diagram of an implantable electrical stimulator with two leads with conformable arrays of electrodes.

FIG. 13 is a schematic diagram of an implantable electrical stimulator 12 with two leads 14A, 14B having lead bodies 16A, 16B with confromable arrays of electrodes 24 at respective distal ends 18A, 18B. In the example of FIG. 8, stimulation pulses can be applied between not only electrodes 24 in an electrode array carried by a single lead 14A, but also between electrodes carried by different leads 14A, 14B. The application of stimulation pulses between electrodes on different leads 14A, 14B further enhances the variety of spatial stimulation sites available for delivery of stimulation pulses. The use of two leads 14A, 14B may be especially useful in spinal cord stimulation (SCS) applications in which each lead extends along a respective side of the spinal cord.

Figure 14:
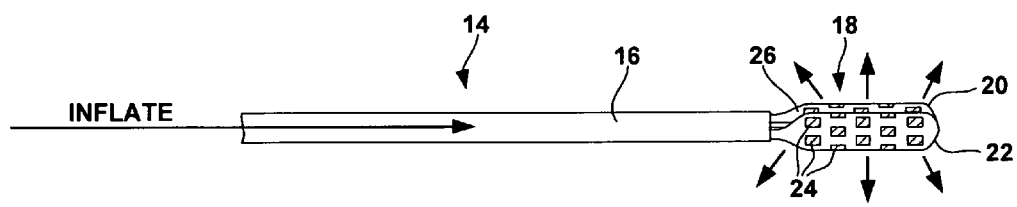
FIG. 14 is a schematic diagram of an implantable lead with an inflatable array of electrodes in a deflated state.
Figure 15:
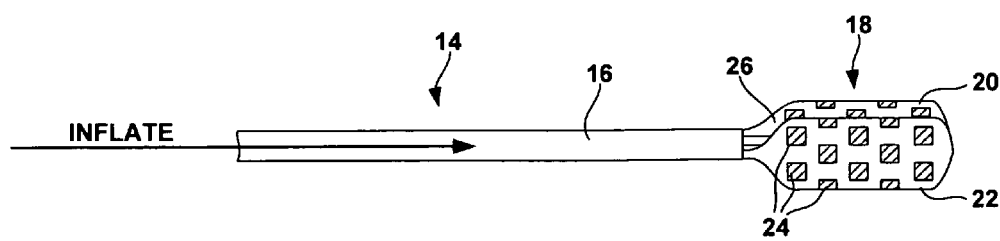
FIG. 15 is a schematic diagram of an implantable lead with an inflatable array of electrodes in an inflated state.

FIGS. 14 and 15 are schematic diagram of an implantable lead 14 with an inflatable, balloon-like array of electrodes. FIG. 14 shows lead 14 in a deflated state, while FIG. 15 shows lead 14 in an inflated state. In the example of FIGS. 14 and 15, lead 14 includes a lead body 16 with a distal end 18 defining an inflatable chamber between concave surface 20 and convex surface 22. The inflatable chamber may be formed, e.g., as a void between layers within the multi-layer manufacturing process described with reference to FIGS. 7 and 8. Lead body 16 defines an inner lumen that serves as an inflation channel for transmission of an inflation fluid into the inflatable chamber of distal end 18. Upon expansion, the spacing between electrodes 24 is increased. In addition, the expanded size of distal end 18 may assist in anchoring the array of electrodes 24 relative to a target stimulation site.

Once lead 14 is placed within a patient, a physician applies the inflation fluid and then closes the inflation channel to maintain the fluid pressure within distal end 18. The inflation channel may be closed, e.g., with a small pin or clamp. The physician then couples the various conductors carried by lead body 16 to appropriate contacts within a stimulator 12. The conductors and electrodes 24 may be insulated from the inflation fluid to prevent electrical shorting. Alternatively, the inflation fluid may be substantially non-conductive of electrical energy.

If explantation is required, the physician may open the inflation channel to withdraw the inflation fluid from distal end 18, facilitating removal of the lead. The inflation fluid, which may be a liquid, gas, or gel, expands distal end 18. Examples of suitable inflation fluids include saline and sterile water. In some embodiments, an inflation fluid such as silicone may be curable, e.g., by heat or radiation, to solidify. However, solidified materials may make non-surgical explanation more difficult than when fluid or semi-fluid materials are used as the inflation fluid.

Figure 16:
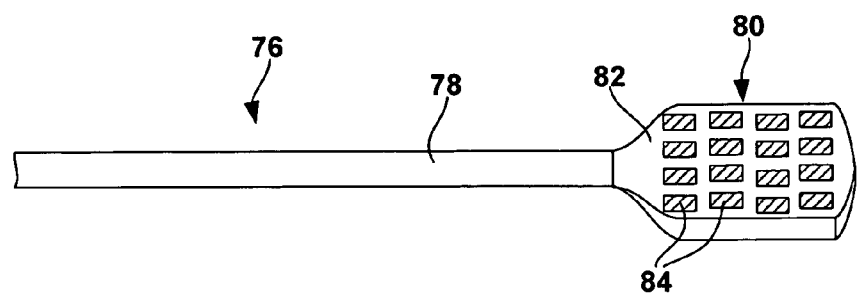
FIG. 16 is a schematic diagram of an implantable lead with a conformable array of electrodes arranged on a pillow-like distal end.

FIG. 16 is a schematic diagram of an implantable lead 76 with lead body 78 and a conformable array of electrodes arranged on a pillow-like distal end 80. In the example of FIG. 16, distal end 80 includes a substantially rectangular paddle 82 carrying an array of electrodes 84 on at least one side of the paddle. Paddle 82 may be formed from flexible, conformable materials as described herein. Unlike conventional paddle leads, paddle 82 may have a pillow-like shape and includes flexible materials designed to promote conformability of the array electrodes 84 to a tissue site. In some embodiments, electrodes 84 may be provide on opposite sides of paddle 82. A multi-layer fabrication process as described with reference to FIGS. 7 and 8 may be used to form distal end 80. The paddle 82 is conformable and compressible to promote surface contact with tissue within a target stimulation site. For example, paddle 82 may be formed from silicone or polyurethane, and filled with a fluid or semi-fluid medium to enhance conformability.

Figure 17:
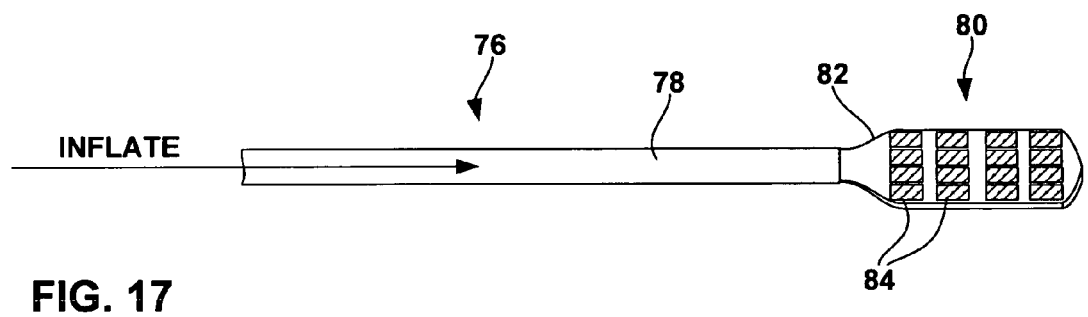
FIG. 17 is a schematic diagram of the implantable lead of FIG. 16 with an inflatable array of electrodes in a deflated state.
Figure 18:
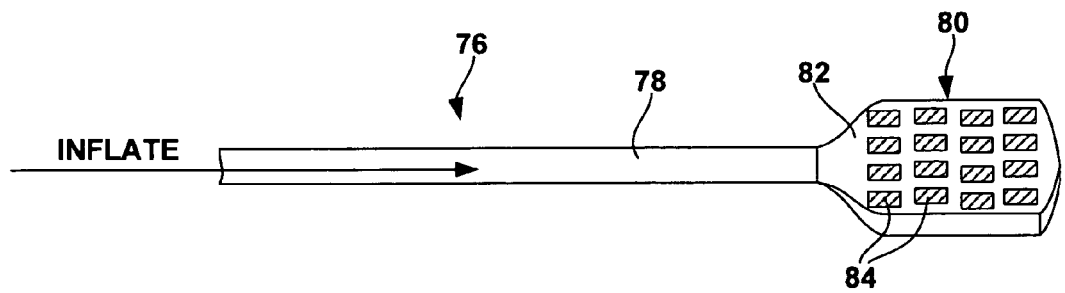
FIG. 18 is a schematic diagram of the implantable lead of FIG. 16 with an inflatable array of electrodes in an inflated state.

FIG. 17 is a schematic diagram of the implantable lead 76 of FIG. 16 with an inflatable array of electrodes 84 in a deflated state. FIG. 18 shows lead 76 with an inflatable array of electrodes 84 in an inflated state. In the example of FIG. 17, paddle 82 at distal end 80 substantially conforms to the arrangement shown in FIG. 16. However, paddle 82 is further constructed to define an interior inflation chamber that is coupled to an inflation channel within lead body 78. In this manner, paddle 82 can be inflated from a small, thin, deflated state (FIG. 17) to a larger, thicker, pillow-like, inflated stated (FIG. 18). The resulting pillow-like array of electrodes 84 is conformable and compressible to cradle target tissue and promote surface contact between electrodes 84 and the tissue. In some cases, the inflation of paddle 82 may contribute to fixation of distal end 80 within the stimulation site.

As an alternative to the inflatable embodiments depicted in FIGS. 14, 15, 17, and 18, a distal end 18 of a lead 14 may include a supporting frame that can be compressed for deployment within the patient, and then permitted to expand when the distal end reaches the stimulation site. For example, a shape memory alloy such as Nitinol may be used to form a support frame for distal end 18. For deployment within a patient, a sheath or introducer may surround the support frame, compressing it inward to provide a smaller diameter that facilitates tunneling. When distal end 18 reaches the target stimulation center, the sheath is withdrawn from the distal end, permitting the supporting frame to expand outward, e.g., under normal elasticity or spring force, or as a function of shape memory properties. In either case, the sheath constrains the supporting frame for deployment. Upon withdrawal of the sheath, the supporting frame is released, permitting distal end 18 to assume its intended size and shape.

Various embodiments of the described invention, including stimulator 12, may include processors that are realized by microprocessors, Application-Specific Integrated Circuits (ASIC), Field-Programmable Gate Arrays (FPGA), or other equivalent integrated or discrete logic circuitry. The processor may also utilize several different types of data storage media to store computer-readable instructions for device operation. These memory and storage media types may include any form of computer-readable media such as magnetic or optical tape or disks, solid state volatile or nonvolatile memory, including random access memory (RAM), read only memory (ROM), electronically programmable memory (EPROM or EEPROM), or flash memory. Each storage option may be chosen depending on the embodiment of the invention.

Many embodiments of the invention have been described. Various modifications may be made without departing from the scope of the claims. For example, although the invention has been generally described in conjunction with implantable neurostimulation devices, it may also be used with other implantable medical devices, such as electrical muscle stimulation devices, and functional electrical stimulation (FES) devices. These and other embodiments are within the scope of the following claims.

The invention claimed is:
1. An implantable electrical stimulation lead comprising:
    a lead body extending between a proximal end and a distal end;
    a plurality of electrical conductors within the lead body; and
    a plurality of stimulation electrodes, each of the electrodes being coupled to at least one of the conductors,
    wherein a cross-section of the distal end taken in a direction substantially perpendicular to a longitudinal axis of the lead body defines a substantially continuous concave surface and a substantially convex surface, the convex surface being on an opposite side of the cross-section as the substantially concave surface, the electrodes are positioned at various positions on the concave surface and the convex surface, the electrodes comprise conductive pads, the substantially continuous concave surface defines a channel-like region at the distal end, the substantially concave surface comprises a first portion comprising at least one of the electrodes and a second portion that faces toward the first portion and comprises at least one of the electrodes, wherein at least one of the electrodes is positioned on the concave surface but not the convex surface, and wherein an outer width of the cross-section of the distal end is greater than an outer diameter of the lead body.
2. The lead of claim 1, wherein the distal end is flexible and at least partially conformable to a target stimulation site.
3. The lead of claim 1, wherein the distal end defines an inflation chamber that is at least partially inflatable to expand the distal end.
4. The lead of claim 1, wherein the stimulation electrodes include at least sixteen stimulation electrodes.
5. The lead of claim 1, wherein the distal end is formed at least partially from an elastomeric material.
6. The lead of claim 1, further comprising one or more sensing electrodes positioned on at least one of the concave surface or the convex surface of the distal end.
7. The lead of claim 1, wherein the distal end is configured to compress inward toward a longitudinal axis of the lead body.
8. An implantable electrical stimulator comprising:
    an implantable pulse generator that generates electrical stimulation pulses; and
    an implantable lead coupled to the implantable pulse generator, the lead including a lead body extending between a proximal end and a distal end, a plurality of electrical conductors within the lead body, and a plurality of stimulation electrodes, each of the electrodes being coupled to at least one of the conductors,
    wherein a cross-section of the distal end taken in a direction substantially perpendicular to a longitudinal axis of the lead body defines a substantially continuous concave surface and a substantially convex surface, the convex surface being on an opposite side of the cross-section as the substantially concave surface, the electrodes are positioned at various positions on the concave surface and the convex surface, the electrodes comprise conductive pads, the substantially continuous concave surface defines a channel-like region, the concave surface comprises a first portion comprising at least one of the electrodes and a second portion that faces toward the first portion and comprises at least one of the electrodes, wherein at least one of the electrodes is positioned on the concave surface but not the convex surface, and wherein an outer width of the cross-section of the distal end is greater than an outer diameter of the lead body.
9. The stimulator of claim 8, wherein the distal end is flexible and at least partially conformable to a target stimulation site.

10. The stimulator of claim 8, wherein the distal end defines an inflation chamber that is inflatable to expand the distal end.

11. The stimulator of claim 8, wherein the stimulation electrodes include at least sixteen stimulation electrodes.

12. The stimulator of claim 8, wherein the distal end is formed at least partially from an elastomeric material.

13. The stimulator of claim 8, further comprising one or more sensing electrodes positioned on at least one of the concave surface or the convex surface of the distal end.

14. The stimulator of claim 8, wherein parameters of the electrical stimulation pulses are selected to alleviate symptoms of one or more of chronic pain, a gastrointestinal disorder, a urinary tract disorder, or sexual dysfunction.

15. A method comprising applying electrical stimulation pulses to a patient via an implanted lead, wherein the lead comprises a lead body extending between a proximal end and a distal end, a plurality of electrical conductors within the lead body, and a plurality of stimulation electrodes, each of the electrodes being coupled to at least one of the conductors, wherein a cross-section of the distal end taken in a direction substantially perpendicular to a longitudinal axis of the lead body defines a substantially continuous concave surface and a substantially convex surface, the convex surface being on an opposite side of the cross-section as the substantially concave surface, the electrodes are positioned at various positions on the concave surface and the convex surface, the electrodes comprise conductive pads, the substantially continuous concave surface defines a channel-like region, the concave surface comprises a first portion comprising at least one of the electrodes and a second portion that faces toward the first portion and comprises at least one of the electrodes, wherein at least one of the electrodes is positioned on the concave surface but not the convex surface, and wherein an outer width of the cross-section of the distal end is greater than an outer diameter of the lead body.

16. The method of claim 15, further comprising positioning the distal end of the lead body proximate a target nerve site within the patient.

17. The method of claim 15, wherein the target nerve site and parameters of the electrical stimulation pulses are selected to alleviate symptoms of one or more of chronic pain, a gastrointestinal disorder, a urinary tract disorder, or sexual dysfunction.

18. The method of claim 15, wherein the distal end is flexible and at least partially conformable to a target stimulation site.

19. The method of claim 15, wherein the stimulation electrodes include at least sixteen stimulation electrodes.

20. The method of claim 15, wherein the distal end is formed at least partially from an elastomeric material.

21. The method of claim 15, wherein the lead further comprises one or more sensing electrodes positioned on at least one of the concave surface or the convex surface of the distal end, the method further comprising sensing at least one electrical signal via the sensing electrodes.

22. The method of claim 15, wherein the distal end defines an inflation chamber that is at least partially inflatable, the method further comprising inflating the inflation chamber upon deployment of the distal end of the lead within the patient to expand the distal end.

23. An implantable electrical stimulation lead comprising:
a lead body extending between a proximal end and a distal end;
a plurality of electrical conductors within the lead body; and
a plurality of stimulation electrodes, each of the electrodes being coupled to at least one of the conductors,
wherein the distal end is substantially pliant and conformable to a target stimulation site, the distal end comprising a substantially continuous concave surface, wherein the substantially continuous concave surface comprises a first portion and a second portion that define a channel-like region, and wherein the plurality of stimulation electrodes comprises a first electrode comprising a first conductive pad positioned on a first surface of the first portion of the distal end but not a second surface of the first portion of the distal end, a second electrode comprising a second conductive pad positioned on the second surface of the first portion of the distal end but not the first surface of the first portion of the distal end, the second surface being on an opposite side of the first portion as the first surface, a third electrode comprising a third conductive pad positioned on the second portion of the distal end, and wherein an outer cross-sectional width of the distal end that defines the substantially concave surface is greater than an outer diameter of the lead body.

24. The lead of claim 23, wherein the distal end defines an inflation chamber that is at least partially inflatable to expand the distal end.

25. The lead of claim 23, wherein the stimulation electrodes include at least sixteen stimulation electrodes.

26. The lead of claim 23, wherein the distal end is formed at least partially from an elastomeric material.

27. The lead of claim 23, further comprising one or more sensing electrodes positioned on the concave surface of the distal end.

28. The lead of claim 23, wherein the distal end has a pillow-like shape.

29. An implantable electrical stimulation lead comprising:
a lead body extending between a proximal end and a distal end;
a plurality of electrical conductors within the lead body; and
a plurality of stimulation electrodes, each of the electrodes being coupled to at least one of the conductors,
wherein the distal end defines a substantially continuous concave surface that comprises a first distal portion and a second distal portion extending from the lead body, the first and second distal portions defining a channel-like region, and wherein the electrodes are positioned at various positions on each of the first and second distal portions, the plurality of stimulation electrodes comprising a first electrode comprising a first conductive pad positioned on a first surface of the first distal portion but not a second surface of the first portion of the distal end, and a second electrode comprising a second conductive pad positioned on the second surface of the first distal portion but not the first surface of the first portion of the distal end, the second surface being on an opposite side of the first distal portion as the first surface, and wherein an outer cross-sectional width of the distal end that defines the substantially concave surface is greater than an outer diameter of the lead body.

30. The lead of claim 29, wherein the distal end is flexible and at least partially conformable to a target stimulation site.

31. The lead of claim 29, wherein the stimulation electrodes include at least sixteen stimulation electrodes.

32. The lead of claim 29, wherein the stimulation electrodes comprise conductive pads.

33. The lead of claim 29, wherein the distal end is formed at least partially from an elastomeric material.

34. The lead of claim 29, further comprising one or more sensing electrodes positioned on the concave surface of the distal end.

* * * * *